(12) United States Patent
Berger

(10) Patent No.: US 7,333,013 B2
(45) Date of Patent: Feb. 19, 2008

(54) MEDICAL IMPLANT DEVICE WITH RFID TAG AND METHOD OF IDENTIFICATION OF DEVICE

(76) Inventor: J. Lee Berger, 895 Mohawk Rd., Franklin Lakes, NJ (US) 07417

( * ) Notice: Subject to any disclaimer, the term of this patent is extended or adjusted under 35 U.S.C. 154(b) by 113 days.

(21) Appl. No.: 10/840,384

(22) Filed: May 7, 2004

(65) Prior Publication Data

US 2005/0247319 A1    Nov. 10, 2005

(51) Int. Cl.
*G08B 1/08* (2006.01)
*H04Q 7/00* (2006.01)

(52) U.S. Cl. ............... 340/539.12; 340/572.8; 235/375; 607/2

(58) Field of Classification Search ........... 340/539.12, 340/572.1, 572.8; 235/375, 376, 385; 600/300; 607/2
See application file for complete search history.

(56) References Cited

U.S. PATENT DOCUMENTS

| | | | | |
|---|---|---|---|---|
| 5,423,334 A | * | 6/1995 | Jordan | 128/899 |
| 6,111,520 A | * | 8/2000 | Allen et al. | 340/870.16 |
| 6,327,501 B1 | * | 12/2001 | Levine et al. | 607/27 |
| 6,385,593 B2 | * | 5/2002 | Linberg | 705/28 |
| 6,442,432 B2 | * | 8/2002 | Lee | 607/59 |
| 6,766,200 B2 | * | 7/2004 | Cox | 607/60 |
| 2002/0158120 A1 | * | 10/2002 | Zierolf | 235/375 |
| 2003/0155413 A1 | * | 8/2003 | Kovesdi et al. | 235/375 |
| 2005/0022581 A1 | * | 2/2005 | Sunshine | 73/31.05 |
| 2005/0258242 A1 | * | 11/2005 | Zarembo | 235/385 |

* cited by examiner

Primary Examiner—Benjamin C. Lee
Assistant Examiner—Travis R. Hunnings
(74) Attorney, Agent, or Firm—John S. Hale; Gipple & Hale

(57) ABSTRACT

The present invention is directed a method of making an interactive medical implant device including a radio frequency identification tag mounted to an implant, the tag being covered with a liquid impermeable seal. Identification of the RFID tag allows the physician to identify the specific identified implant with a an instrument model or patient database and allows the physician access to desired pertinent information regarding the medical implant device.

7 Claims, 2 Drawing Sheets

MEDICAL IMPLANT DEVICE WITH RFID TAG AND METHOD OF IDENTIFICATION OF DEVICE

RELATED APPLICATIONS

There is no related application.

FIELD OF INVENTION

The present invention relates generally to a method of determining the manufacturer and model of a medical implant device after implantation and to construction of a medical implant device employing an RFID tag on a surface of the medical implant.

BACKGROUND OF THE INVENTION

Radiofrequency identification (RFID) is a type of automatic identification technology that uses low wattage radio frequency transmission for identification and data cataloguing. Radiofrequency identification (RFID) accelerates and facilitates the collection of data and eliminates the need for human operations in the process. Radiofrequency identification (RFID) uses a reader and antenna array which generates an EM-field from 850 MHz and 2 GHz and special tags which respond to the EM-field with the emission of data are attached or embedded to an object. There are no moving parts in radiofrequency identification (RFID) tags and readers and the systems are able to operate effectively for extended periods without maintenance. The broadcasted radio frequency waves do not require a direct line of sight and locate objects in a three dimensional orientation and will travel through non-metallic materials.

Radiofrequency identification tags can be manufactured in various shapes, sizes and configurations to suit an intended purpose. The no contact, non-line-of-sight nature of the technology and its speed are important advantages of radiofrequency identification (RFID) systems. A tag and reader communicate in most cases with a response in less than 100 milliseconds and radiofrequency identification (RFID) tags can be read through environmentally challenging conditions. The tags can work in a temperature range from −40° C. to +200° C. and are very durable and resistant to wear.

Passive radiofrequency identification (RFID) tags are typically read-only tags programmed with a unique set of data that cannot be modified. This awards a high level of security. Passive radiofrequency identification (RFID) tags operate without a separate external power source and obtain operating power generated from the exciter/reader. Passive tags are small, inexpensive, currently ranging from 25¢ to 50¢, and are expected to rapidly drop in price to 5¢or less, and offer a theoretically unlimited operational lifetime. The tags will usually last longer than the object to which they are attached. A passive radiofrequency tag does not add to any radiofrequency energy already in the environment.

The development of radio frequency identification, called RFID, integrated circuitry and the adoption of a standardized EPC (electronics product code) in late 2003 has permitted use of RFID tags in a wide range of applications. Use of such arrangements in a product package has a wide variety of applications, including inventory, product processing, and tamper-indication, by monitoring the unique tag of the product package.

Radiofrequency identification tags are currently used for identifying and locating animals. The application created for animal identification is invaluable for farmers and pet owners. Animal tracking tags, inserted under the skin of an animal, are only a few millimeters in size. The specific identification coded in tag is recorded in a database. This system can monitor the animal's identity, location, type of diet, and living conditions.

The microelectronics assembly is configured for radio frequency interaction by the provision of a suitable radio frequency identification (RFID) integrated circuit currently placed on a silicon chip the size of a grain of sand, an antenna, and one or more interconnections operatively connecting the circuit and the antenna. The resulting assembly is commonly referred to as an RFID tag.

A radiofrequency identification system consists of three major components; comprising a reader (or interrogator), its associated antenna and the transponders (radio frequency tags, /RFID Cards) that carry the unique programmed data and a computer or other system for processing data which is read by a reader.

The reader transmits a low-power radio signal generally, under 3 watts, through its antenna, that the tag receives via its own antenna to power an integrated circuit (chip). Using the energy it gets from the signal when it enters the radio field, the tag will briefly converse with the reader for verification and the exchange of data. Once that data is received by the reader it can be sent to a controlling computer for processing and management.

A radiofrequency identification tag contains an electronic chip as a principal element, which is controlling the communication with the reader. This contains a section of memory functioning to store the identification codes or other data; the memory being accessed at the communication time. The RFID tags can be attached or integrated in the objects for identification.

The present invention is directed to a RFID tag embedded or mounted into an implantable medical device for the identification of the medical device as to manufacturer and model, for determination of global positioning of the device and identifying the instruments used to insert and remove the medical device. For example in total joint replacement, if the medical implant device is embedded with a radiofrequency identification tag (RFID) the surgical implantation of the device could be monitored by a global positioning navigational system. The implanted device could be serially monitored for any change in alignment, wear or loosening during the lifetime of the implant. Radiofrequency identification tags (RFID) are virtually impossible to copy. Radiofrequency identification technology can easily be adopted for medical confidentiality.

SUMMARY OF THE INVENTION

The present invention is directed toward a method for integrating labeling of implantable medical devices and management of medical information comprising the steps of: labeling the medical device with a radiofrequency identification device (RFID) and maintaining a medical product database which associates the information, including manufacturer, type of implant, composition of implant, dimensions and measurements of implant, date of implantation, expiration date if applicable, type of instruments required for removal of implant and any other type of data that may be beneficial, with the specific tag identification for use by the physician or surgeon. The invention is also directed toward a medical implant with an RFID tag and/or patient information database including patient name, address, medical history, treating physicians and institution, implanted device history.

It is an object of the invention to integrate radiofrequency identification (RFID) tags with implantable medical devices for automatic device identification, monitoring and patient information.

It is another object of the invention to use radiofrequency identification (RFID) to provide more exact implant information and improved data acquisition regarding the implant.

It is still another object of the invention to use radiofrequency identification (RFID) of implantable medical devices to improve the access and control of critical medical information.

It is yet another object of the invention to specify and accurately identify medical implants by using radiofrequency identification (RFID) tags placed upon the medical implant.

It is another object of the invention to provide radiofrequency identification (RFID) tags on implants that are substantially maintenance and error free.

It is another object of the invention to use radiofrequency identification (RFID) tags can be read through aqueous environment of the human body.

It is yet another object of invention to use radiofrequency identification (RFID) tags for monitoring of the implanted device.

It is another object of the invention to utilize radiofrequency identification (RFID) tags to control electrical stimulation, magnetic stimulation, and administration of pharmaceutical or other therapeutic modalities.

It is also an object of the invention to utilize radiofrequency identification (RFID) tags on medical implants to prevent counterfeiting of the implants or reusing the same in other patients.

It is yet another object of the invention to utilize radiofrequency identification (RFID) of implantable medical devices to facilitate increased efficiency and productivity and of related patient information.

These and other objects, advantages and novel features of the present invention will become apparent when considered with the teaching contained in the detailed disclosure along with the accompanying drawings.

DETAILED DESCRIPTION OF THE INVENTION

Figure 1:
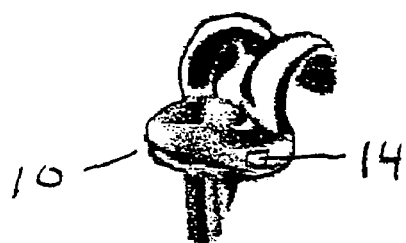
FIG. 1 is a perspective view of a medical implant with an RFID tag placed thereon.

While the present invention is susceptible of embodiment in various forms as is shown in the drawings, and will hereinafter be described, a presently preferred embodiment, with the understanding that the present disclosure is to be considered as an exemplification of the invention, and is not intended to limit the invention to the specific embodiments disclosed herein.

The present invention is directed to a medical implant with an associated RFID tag and a method of making an interactive medical implant which is sealed against liquid engagement with a radio frequency identification integrated circuit and associated antenna disposed on or within the implant. It is envisioned that the medical implants which will be used are those implants currently used in orthopaedics and cardiac procedures. Orthopaedic implants can consist of implants for joint replacement, implants for hip replacement, implants for knee replacement, implantable spinal cages, implantable spinal plates, implantable bone plates and bone screws; implantable rods, implantable nails, implantable bone screws, and implantable bone stents. Cardiac implants can consist of cardiac and vascular stents, pacemakers and defibrillation devices. One problem which occurs with pacemakers in addition to the insertion and operation of same is a problem of selling used pacemakers or recalled pacemakers for reinsertion into new patients. The tagged medical implant facilitates its use for a variety of applications, including product identification after implantation, recipient medical identification, storage and dissemination of product processing information, and product quality assurance, including verification of manufacturers and original equipment. Use of medical implants formed in accordance with the present invention permits efficient inventory control.

Figure 2:
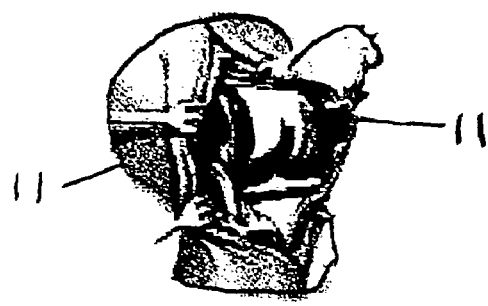
FIG. 2 is the medical implant of FIG. 1 implanted in the knee of a human patient.

As illustrated in FIG. 2, the implant 10 which can be formed in accordance with the present invention comprises seal or pouch 12 of a waterproof biocompatible plastic and an associated RFID tag 14 having an integrated circuit 16 and antenna 18.

The RFID tag 14 includes a radio frequency identification integrated circuit 16 in semiconductor chip form which is about the size of a grain of sand electrically connected to an antenna 18 placed in contrast with the semiconductor circuit and mounted on a substrate 15. The RFID tag when placed on medical implant 10 is covered by a plastic seal or closure 12 which acts as a moisture impermeable barrier protecting the circuit against body fluids and damage. The chip is of standard construction and can be obtained from Alien Inc. or Matrix, Inc. which are several of many chip manufacturers in the RFID chip industry. The antenna 18 is operatively connected to the integrated circuit 16, with the antenna cooperating with the integrated circuit to permit the integrated circuit to be externally powered without physical connection of a power supply thereto. The antenna 18 provides the desired radio frequency interface with an associated radio frequency input/output device 20 (FIG. 3) which can be configured to provide remote RF to the tag 14 and/or reading and retrieval of electronic information carried by the integrated circuit 16 by the reader 22.

In accordance with the present disclosure, it is contemplated that the integrated circuit 16 and antenna 18, and any associated components, including interconnections with the integrated circuit, be positioned within the seal 12 by disposition of the electronic components on a substrate or liner 15 which is inserted into or covered by the seal 12.

External powering of the integrated circuit 16 precludes the need for an internal power supply operatively connected to the integrated circuit for providing electrical power thereto. However, for some configurations of the present package (such as providing for capturing continuous historical data such as pressure and/or temperature), it may be desirable to provide an alternate compact power supply 24, such as diagrammatically illustrated in FIG. 3, which is operatively connected to the integrated circuit 16.

Figure 3:
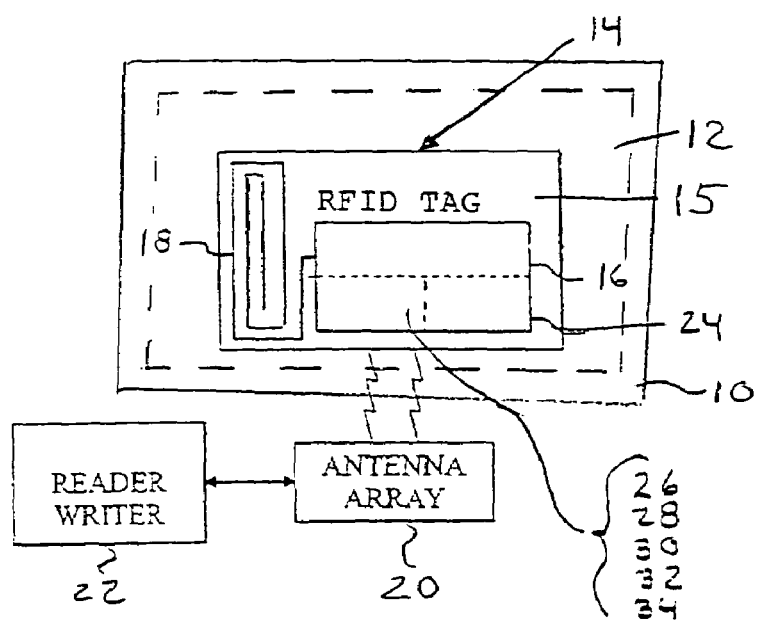
FIG. 3 is a schematic representation of a medical implant RFID tag being excited by a reader and the identification information of the tag being received.

The microelectronics assembly of the package can be configured to include one or more different types of compact-size (i.e., micro) sensing or medical treatment devices. Such sensing devices are in the form of a microchip circuit and may include, by way of example, a pressure sensor 26, a temperature sensor 28, a chemical sensor 30 for sensing the presence of chemicals such as oxygen, and/or a biological sensor 32 for sensing the presence of microorganisms or a micro wave form generator 34 for generating electronic energy in the range of 20-50 microamps to heal the area in the patient surrounding the implant 10. While the above noted sensors (26-32) are known in the art, the use of same with RFID tags has not been used. The configuration of the circuit 16 and antenna 18 with one or more of the internal sensor devices noted above greatly enhances versatile use of the medical implant, including determination of the manufacturer of the implant, years after implantation, allowing the medical history of the patient to be displayed after reading the implant identification code, anti-counterfeiting and preventing the use of used medical implants. An array of sensors can be provided for certain applications, with the array preferably integrated with radio frequency integrated circuit 16 as is schematically shown in FIG. 3.

It is contemplated that the microelectronics assembly used in practicing the present invention can be positioned on a mounting substrate 15 inserted into the seal or pouch 12 made of durable biocompatible plastic with the seal 12 in turn being secured by biocompatible cements, adhesives or glue to the sterile medical implant device. The RFID tag is positioned in an area which is not subject to wear by engagement with surrounding various body parts. The present invention particularly contemplates that the mounting substrate for the microelectronics be provided in the form of a substrate or liner 15 for insertion into the seal or pouch 12. The RFID tags 14 are preferably are inserted into pre-molded closures or seals 12 (as opposed to in situ molding of a liner). Closure manufacturers typically use thin sheet material ranging from 0.015 to 0.030 inches thick, depending upon the particular closure design. This material is supplied in large rolls, and is typically fed into punching machines that punch circular discs from the lining material, and substantially simultaneously insert the punched discs into closure shells. The remaining "skeleton" is typically re-ground and returned to the material supplier for recycling and inclusion in future rolls of lining material.

In such an arrangement, the sealing liner thus acts to provide the desired sealing engagement between the closure assembly and the medical implant devices, with the microelectronics assembly thus securely positioned within the closure, yet isolated from the fluids of the body after implantation, in accordance with FDA requirements.

The present invention contemplates that various techniques can be employed for providing the antenna 18, and associated interconnections, on the mounting substrate 15 for the electronics assembly. In one form, the antenna and interconnections are printed on the substrate 15 with electrically conductive inks, with the printing steps selected from the group consisting of ink jet printing, silk screen printing, and offset printing. Alternatively, the antenna and interconnections can be formed by thin film deposition utilizing evaporation or sputtering on the mounting substrate, with etching or laser machining of the thin film effected to form the antenna and interconnections.

Other techniques can be employed in accordance with the present invention for formation of the antenna and interconnections of the microelectronics assembly. The antenna and interconnections can be formed by lamination on the mounting substrate, with the lamination etched or laser machined for formation of the antenna and interconnections. Laser "writing" can be employed through the use of organometallic gas which forms metal deposits when subjected to laser light.

Mounting of the integrated circuit 16 on the mounting substrate can also be effected in various ways. As is known by those skilled in the art, the integrated circuit can be positioned active-side-down on the mounting substrate with connection from the pads on the integrated circuit made directly to the antenna or interconnection by soldering, stud-bump bonding or with a conductive adhesive, or active-side-up on the substrate with connection from the pads on the integrated circuit made directly to the antenna or interconnection with wire bonds. Formation of the microelectronics assembly can include the steps of first positioning the integrated circuit on the mounting substrate, and forming a planarization layer over the integrated circuit. One or more openings are then formed in the planarization layer, such as by photolithography or laser machining. The antenna is then formed on the planarization layer, and interconnections formed through the openings in the layer. The antenna and interconnections can be formed by metal deposition followed by photolithography.

It is within the purview of the present invention that the microelectronics assembly can be positioned on the mounting substrate by printing the integrated circuit with semiconductor inks as well as the associated antenna and interconnections with electrically-conductive inks directly on the.

To facilitate efficient use of the present interactive information package, it is contemplated that the apparatus employed for insertion of the microelectronics and mounting substrate into the associated closure be a so-called "smart machine", that is, capable of reading information from, and writing information onto, the microelectronics assembly. It is particularly contemplated that this apparatus be configured for testing the installed microelectronics prior to shipment of the RFID tags.

Figure 4:
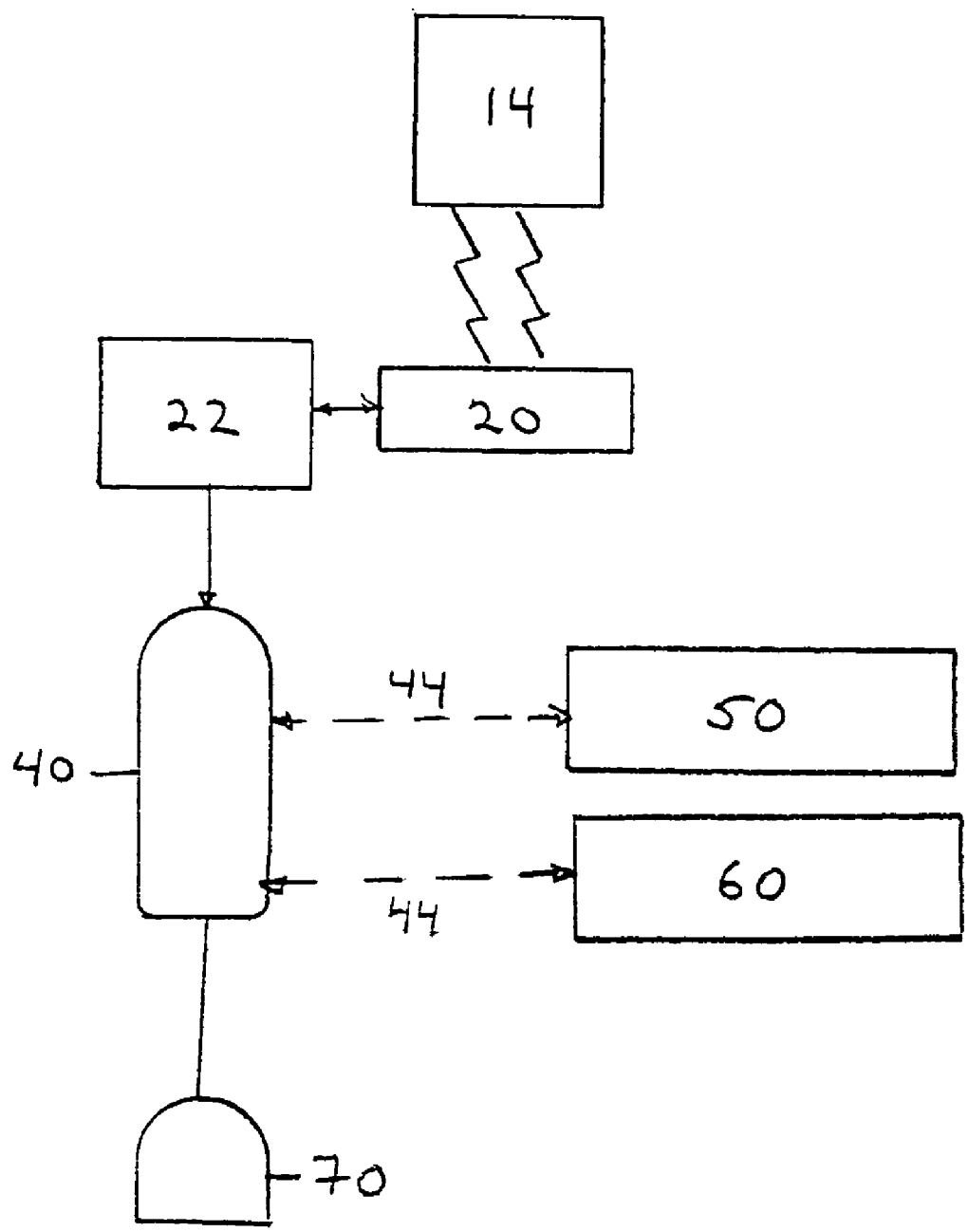
FIG. 4 is a schematic representation of a medical implant RFID tag being excited by a reader antenna with the specific implant information going to data base and connected with product information and/or patient medical information.

In operation as shown in FIG. 4 the sterile medical implant 10 is implanted into a patient 11 with an RFID tag affixed thereto which has a specific identifying code. The tag 14 is accessed by exciting the same in a field ranging from 870 Mhtz to 990 Mhtz at a power of up to three watts generated by an outside powered antenna 20. The RFID tag 14 emits a binary code which is read by a reader 22 and the reader 22 transmits the code to a computer 40 which accesses a data base 50 by the internet 44 to link the code generated specific to the medical implant to a specific manufacturer. Upon determination of the manufacturer of the medical implant and model of the medical implant, the surgeon or physician can then click up the diagrams and schematics for the medical implant or alternatively link the code of the medical implant to a database 60 of a specific patient in which the device has been implanted and pull up the file history for the patient including records and/or pictures of the implant operation as well as the medical history of the patient so that the data is stored and displayed on terminal 70 of the user or physician.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. A method of making an interactive medical sterile orthopaedic implant, comprising the steps of:
   a) placing a microelectronics assembly, including an RFID integrated circuit, an antenna, and one or more interconnections operatively connecting said circuit and said antenna and a wave form generator connected to said integrated circuit on a sterile orthopedic implant;
   b) inserting said sterile orthopaedic implant into a patient;
   c) activating said generator to generate electronic energy in the range of 20-50 microamps in the patient for a period of time to accelerate healing in the patient; and
   d) repeating step c) a plurality of times during the implant healing process.

2. A sterile orthopaedic medical implant comprising a sterile medical orthopedic implant, an RFID tag including a chip having an integrated circuit and an antenna connected to said integrated circuit-secured to said orthopaedic implant, and a biocompatible cover placed over said RFID tag and secured to said chip which is impermeable to liquid precluding liquid from engaging said RFID tag, a sterile generator connected to said integrated circuit and mounted on said implant which when energized generates electronic energy in the range of 20-50 microamps to accelerate healing of tissue in the patient receiving said sterile medical orthopedic implant.

3. A sterile medical implant in accordance with claim 2 wherein said sterile medical orthopaedic implant is taken from a group consisting of implants for joint replacement, implants for hip replacement, implants for knee replacement, implantable spinal cages, implantable spinal plates, implantable bone plates, implantable rods, implantable nails, implantable bone screws and implantable bone stents.

4. A sterile medical implant in accordance with claim 2 wherein said RFID integrated circuit is in electrical connection with a sterile pressure sensing means.

5. A sterile medical implant in accordance with claim 2 wherein said RFID integrated circuit is in electrical connection with a sterile chemical sensing means.

6. A sterile medical implant in accordance with claim 2 wherein said RFID integrated circuit is in electrical connection with a sterile microorganism sensing means.

7. A sterile medical implant in accordance with claim 2 wherein said RFID integrated circuit is in electrical connection with a sterile temperature sensing means.

* * * * *